United States Patent [19]

Wood et al.

[11] Patent Number: 4,540,410

[45] Date of Patent: Sep. 10, 1985

[54] LYOPHILIZED COMPOSITIONS, PREPARATION AND USE THEREOF

[75] Inventors: Grace Wood, N. Scituate; Benjamin R. Duce, Westborough; Russell W. Pelham, Hull; James Woiszwillo, Milford, all of Mass.

[73] Assignee: Serono Pharmaceutical Partners, Randolph, Mass.

[21] Appl. No.: 442,151

[22] Filed: Nov. 16, 1982

[51] Int. Cl.$^3$ .......................... F26B 5/06; A61M 3/00
[52] U.S. Cl. ............................................ 604/56; 34/5; 604/82; 604/187; 604/290; 604/311
[58] Field of Search .................. 34/5; 604/82, 83, 84, 604/85, 86, 87, 88, 89, 90, 91, 92, 56, 187, 310, 311, 289, 290, 403, 416, 414

[56] References Cited

U.S. PATENT DOCUMENTS

| 2,380,339 | 7/1945 | Siedentopf | 34/5 |
|---|---|---|---|
| 3,743,714 | 7/1973 | Deutsch | 34/5 |
| 4,006,220 | 2/1977 | Gottlieb | 424/101 |
| 4,061,731 | 12/1977 | Gottlieb | 424/101 |
| 4,167,945 | 9/1979 | Gottlieb | 424/101 |
| 4,191,751 | 3/1980 | Gottlieb | 424/319 |

Primary Examiner—John J. Camby
Attorney, Agent, or Firm—Ostrolenk, Faber, Gerb & Soffen

[57] ABSTRACT

A syringe containing a lyophilized mixture of an absorbable gelatin powder and aminocaproic acid is prepared by mixing the gelatin powder, aminocaproic acid and water to form a slurry, introducing an aliquot of the slurry into a syringe and freeze-drying the slurry in the syringe.

20 Claims, No Drawings

LYOPHILIZED COMPOSITIONS, PREPARATION AND USE THEREOF

BACKGROUND OF THE INVENTION

Several techniques have been employed to correct depressed ovoid and linear cutaneous scars. These scars may have been associated with acne vulgaris, varicella, herpes, trauma, surgery, frown lines and wrinkles. Presently available treatments have definite disadvantages. Dermabrasion and chemical peel which involve lowering of the tissue surrounding the scar requires a long convalescence and avoidance of sun for 6 months. Plastic surgery also require long convalescence and is very expensive. Silicone implants have a tendency to migrate, form permanent papules, and peau d'orange and overcorrection frequently occurs. The bovine collagen implant, Zyderm, requires a skin sensitivity test, several treatments and refrigerated storage.

Sheldon K. Gottlieb in U.S. Pat. Nos. 4,006,220 and 4,061,731 describes a new composition which is useful for the repair of depressed cutaneous scars which comprises at least one fibrin stabilizer and plasma. The fibrin stabilizer can be a pulverized absorbable gelatin sponge, aminocaproic acid or derivatives thereof, and preferably a combination of the pulverized and aminocaproic acid. Dr. Gottlieb has also shown in U.S. Pat. Nos. 4,167,945 and 4,191,751 that this composition can also be used to enhance the healing of grafted tissue or to promote the growth of new connective tissue over surface wounds.

The Gottlieb composition is prepared by mixing the absorbable sponge, aminocaproic acid and the patient's plasma to obtain the desired composition which is then introduced into a suitable administration device such as a syringe for administration to the patient. The composition, however, is extremely viscous and difficult to introduce into the syringe. The mixture also has a tendency to separate and dry out. In addition, it is difficult to maintain sterility while storing and mixing the three components.

Since each patient's plasma is unique, it is not possible to provide a physician with a premixed Gottlieb composition. The problem could be resolved by providing a mixture of pulverized gelatin sponge and aminocaproic acid solution to which the physician can add the patient's plasma. Stability of the mixture, however, remains a major disadvantage. Although shelf-life of a product may often be extended by freeze-drying (lyophilization), the nature of the mixture of pulverized gelatin sponge and aminocaproic acid solution mitigates against such a procedure.

A mixture of the absorbable sponge and aminocaproic acid is a sol-gel, i.e., it lies at the phase boundary between a solution and a gel, and is very viscous, heterogeneous and contains a large amount of entrained air. Such a mixture causes a phenomenon during lyophilization known as "bumping". As the vacuum is drawn, the air bubbles in the material being treated are drawn to the surface very quickly and water is drawn off violently carrying solid material with it. This can be minimized by lyophilizing shallow layers of the material spread over a large surface area so that the bumping is randomized and the amount of material lost as a result is, hopefully, statistically insignificant. Such a procedure, however, is quite time consuming and adds significant cost to preparation of the product. Bumping is particularly sever when the surface area is small such as is encountered in a syringe.

It is accordingly the object of this invention to provide a new and economical method of preparing a lyophilized mixture of absorbable powder and aminocaproic acid in administration syringes and also to provide a method for mixing the lyophilized mixture with the patient's plasma. These and other objects of the invention will become apparent to those skilled in this art from the following detailed description.

SUMMARY OF THE INVENTION

This invention relates to the preparation of a formulation of absorbable gelatin powder and aminocaproic acid which can be easily introduced into an administration syringe and lyophilized; and a method for mixing the lyophilized material with plasma.

More particularly, a free-flowing slurry of absorbable gelatin powder and aminocaproic acid is prepared by mixing the gelatin powder and aminocaproic acid with water. This slurry is easily introduced into a syringe and lyophilized. The patient's plasma is introduced into another syringe mixed with saline and the contents of the syringes are injected back and forth between the two syringes until the desired treatment suspension has been obtained.

DESCRIPTION OF THE INVENTION

In accordance with the present invention, it has been found that a slurry of the absorbable gelatin powder and aminocaproic acid can be lyophilized in an administration syringe without significant bumping. This discovery was particularly surprising in view of the fact that the exposed surface area in a syringe is very small, particularly compared to the depth of the material being lyophilized within the syringe. The exposed surface area (syringe diameter) to depth ratio is generally at least 1:1 and usually at least about 1:2. It would be expected to loose 50% or even more of the slurry within the syringe using standard lyophilizing techniques. Attempts to lyophilize an aqueous solution of the aminocaproic acid per se did result in the 50% loss of active material. It was surprisingly discovered, however, that lyophilization could be applied to the syringe containing the slurry safely and the loss of active material was only about 0.3%.

The slurry is prepared by mixing suitable amounts of the absorbable gelatin powder, aminocaproic acid and water. The gelatin powder is the sterile, substantially water insoluble, non-antigenic, completely proteolytically digestable pulverized gelatin sponge described in the aforementioned Gottlieb patents. The aminocaproic acid component can be aminocaproic acid per se, such as in the form of an aqueous solution containing a preservative (e.g. 0.9% benzyl alcohol; pH about 6.8 by HCl adjustment). Both of these components are commercially available.

The absorbable gelatin powder can be about 20–90% of the mixture of the powder and aminocaproic acid, but is preferably about 40–60% and most preferably about 50%. In preparing the slurry, the water is usually employed in an amount 1–10 parts, preferably about 2–5 parts, per part of mixture of sponge and aminocaproic acid.

An aliquot of the aqueous slurry is introduced into a glass syringe. In general, about 20–50 mg of the powder and about 12.5–75 mg of the aminocaproic acid can be employed for each 0.3–0.5 cc of plasma. For example, if it has been determined that the volume of the treatment composition will be 2 cc, an amount of slurry containing about 40–100 mg of the powder and about 25–150 mg of the aminocaproic acid is introduced into the syringe.

The aqueous slurry is pre-frozen in the syringe, then placed in the pre-cooled lyophilizer. The water is then drawn off very slowly under vacuum. In general the temperature is reduced to below about −10° C., preferably about −20° C., and a vacuum of about 10 to 50 microns, preferably about 50 microns, is employed at a shelf temperature of 15° C. to 35° C.

In use, a physician will obtain a suitable quantity of the patient's plasma, suitably dilute it (e.g. with an about equal volume of 0.9% aqueous NaCl) and introduce it into a syringe. The syringe containing the plasma solution and the syringe containing the lyophilized mixture are then interconnected through a locking system. The contents are mixed by exchanging the material from one syringe into the other and by operating of the syringe plungers a suitable number of times. This mixing technique has been previously been used for mixing Fruend's adjuvant with a suitable antigen.

In order to further illustrate the present invention, the following non-limiting example is set forth below. It will be appreciated that unless otherwise indicated, all temperatures are degrees Celcius and all parts and percentages are by weight throughout this specification and claims unless otherwise indicated.

Thirteen grams of a commercially available absorbable gelatin powder were placed in a flask and 65 ml of an aqueous aminocaproic acid solution was added to the flask. Distilled water in an amount of 260 ml was added to the flask which was then shaken for 5 to 10 minutes to obtain a slurry. One hundred syringes were each filled an aliquot of the slurry which was then frozen therein. The syringes were placed in a pre-cooled lyophilizing apparatus and a vacuum of about 50 microns was established at a self temperature of 15° C.–35° C. It was determined that the loss of pulverized sponge and aminocaproic acid as a result of the lyophilization was only about 0.3% and the lost material was substantially only the aminocaproic acid.

The syringes were stored at various temperatures and the aminocaproic acid content determined at various times to monitor stability of the lyophilized mixture. The results of these tests indicate lyophilization does not appreciately affect aminocaproic acid and that the freezedried form remains stable at 4° C. and 25° C. for at least 6 months, 35° C. for at least 3 months and at 45° C. for two months.

Various changes and modifications can be made in the process and products of this invention without departing from the spirit and scope thereof. The various embodiments which have been described herein were for the purpose of illustrating the invention but were not intended to limit it.

What is claimed is:

1. A syringe containing a lyophilized mixture of an absorbable gelatin powder and aminocaproic acid.

2. The syringe of claim 1 in which said powder is about 20–90% of the mixture of said powder and aminocaproic acid.

3. The syringe of claim 2 wherein said powder is about 40–60%.

4. The syringe of claim 3 wherein said powder is about 50%.

5. The syringe of claim 1 containing about 0.2–0.3 grams of said lyophilized mixture.

6. A method of preparing a syringe containing a lyophilized mixture of an absorbable gelatin powder and aminocaproic acid which comprises admixing absorbable gelatin powder, aminocaproic acid and water to form a slurry, introducing an aliquot of the slurry into a syringe and lyophilizing the slurry in the syringe.

7. The method of claim 6 wherein the absorbable powder is about 20–90% of the mixture of the powder and aminocaproic acid.

8. The method of claim 7 wherein the powder is about 40–60% and the amount of water is about 1–10 parts per part of mixture of powder and aminocaproic acid.

9. The method of claim 8 wherein the powder is about 50% and in which the water is about 2–5 parts per part of the mixture of powder and aminocaproic acid.

10. The method of claim 6 wherein said aliquot is an amount of the slurry sufficient to yield about 0.3–0.5 grams of the resulting lyophilized mixture.

11. The method of claim 6 wherein said lyophilizing comprises freezing said slurry in the syringe and thereafter drawing off water under vacuum.

12. The method of claim 11 wherein the slurry in the syringe is lyophilized at a temperature below about at least −10° C. and at a vacuum of about 10–50 microns.

13. The method of claim 12 wherein the lyophilizing temperature is about −20° C. and the vacuum is about 50 microns.

14. The method of claim 13 wherein the powder is about 50% of the mixture of powder and aminocaproic acid, the water is about 2–5 parts per part of the mixture of powder and aminocaproic acid, the aminocaproic acid is employed in the form of an aqueous solution containing a preservative, and the aliquot is an amount sufficient to yield about 0.3–0.5 grams of lyophilized product.

15. A method of preparing a composition for repairing depressed cutaneous scars comprising plasma, absorbable gelatin powder and aminocaproic acid which comprises introducing plasma of the patient to be treated into a syringe, interlocking the plasma syringe with the syringe of claim 1, and forcing the contents of one syringe into the other syringe a plurality of times until the desired degree of admixing has been obtained.

16. The method of claim 15 in which the plasma syringe contains about 0.3–0.5 cc plasma and about 0.3–0.5 cc of aqueous NaCl and the syringe of claim 1 contains about 40–100 mg powder and about 25–150 mg aminocaproic acid.

17. The method of claim 16 in which the syringe of claim 1 contains about 60–100 mg of each of said powder and aminocaproic acid.

18. A syringe containing a lyophilized mixture of an absorbable gelatin powder and aminocaproic acid produced by the process of claim 6.

19. The syringe of claim 18 in which said powder is about 20–90% of said mixture of said powder and aminocaproic acid.

20. The syringe of claim 19 in which the amount of said lyophilized mixture is about 0.2–0.3 gram.

* * * * *